United States Patent [19]

Jarolics

[11] Patent Number: 4,773,252
[45] Date of Patent: Sep. 27, 1988

[54] GAS MONITORING EQUIPMENT

[75] Inventor: Gyula Jarolics, Copenhagen, Denmark

[73] Assignee: F. L. Smidth & Co. A/S, Denmark

[21] Appl. No.: 876,244

[22] Filed: Jun. 19, 1986

[30] Foreign Application Priority Data

Jul. 11, 1985 [GB] United Kingdom ............... 8517549

[51] Int. Cl.⁴ ............................................. G01N 1/22
[52] U.S. Cl. ..................... 73/23; 73/863.33; 73/863.31
[58] Field of Search ............... 73/23, 863.31, 863.33

[56] References Cited

U.S. PATENT DOCUMENTS

| 3,043,145 | 7/1962 | Hoffman | 73/863.33 |
|---|---|---|---|
| 3,334,513 | 8/1967 | Thomas | 73/23 |
| 3,444,721 | 5/1969 | Hearn et al. | 73/23 |
| 3,457,787 | 7/1969 | Maatsuch et al. | 73/863.31 |
| 3,748,906 | 7/1973 | Manka | 73/863.33 |
| 3,978,732 | 9/1976 | Dillman | 73/863.31 |
| 4,031,747 | 6/1977 | Blanke | 73/23 |
| 4,099,392 | 5/1978 | Smith et al. | 73/863.33 |
| 4,497,214 | 2/1985 | Ramelot | 73/863.12 |
| 4,517,849 | 5/1985 | Nakahori et al. | 73/863.31 |

Primary Examiner—Stewart J. Levy
Assistant Examiner—Hezron E. Williams
Attorney, Agent, or Firm—Brumbaugh, Graves, Donohue & Raymond

[57] ABSTRACT

Equipment for monitoring the concentration of components in a gas flow has two probes (1,2) located at (63) in the gas flow. Sample gas is drawn through the probes and through pipes (3,4) by a pump (8), and test samples are extracted from the pipes by pumps (11,12) and fed to an analysis line (10). The probes (1,2) work alternately, and, when one is not working, it may be cleaned by blowing air through from a source (9), while the corresponding one of the pipes (3,4) is blocked from the line (10) by valves (13-16).

7 Claims, 2 Drawing Sheets

GAS MONITORING EQUIPMENT

BACKGROUND OF THE INVENTION

The invention relates to a monitoring equipment for the quick and reliable detection of the content at least one gaseous component in a gas flow, e.g. the amount of combustible gasese in the flue gas from ordinary combustion, or from a chemical process, in which a material is heat treated through direct or indirect firing of a fuel which may form part of the material to be treated, or be added separately.

An example of such a chemical process is the so-called calcining or $CO_2$-expulsion from, for instance, cement raw materials, the heat treatment being performed in a reactor, the calciner and the flue gases from the calciner being used for preheating the raw material, and the gases thereafter being dedusted and discharged into the atmosphere.

If, during combustion, the fuel is not completely burnt out the flue gases will contain some combustible gases like CO and $CH_4$ which, when mixed with oxygen-containing air, will present a risk of explosion, not least when the flue gas finally is dedusted in a electrostatic precipitator in which electrical discharges frequently occur.

SUMMARY OF THE INVENTION

It is an object of the invention to provide equipment making it possible quickly and reliably to detect the occurrence of combustible gases in a flue gas. If such a detection is made at a point immediately after the flue gas has left its place of origin it will be possible to cut off the energization of an electrostatic precipitator even before the combustible gas reaches the precipitator, or other source of ignition.

The object is achieved by equipment characterized in having two gas extraction probes which are arranged to extract gas to be sampled from substantially the same location in the gas flow, each probe having its own gas pipe leading to an analysing station; a primary gas pump which is arranged to suck gas from the probes to the analysing station, and preferably having a pump capacity enabling it to draw gas from the location to the analysing station in a preset time; a set of valves which are arranged to block the connection of one or other of the gas pipes alternately to the gas pump and to connect the blocked gas pipe to a compressed air system for blowing clean the probe of the respective gas pipe; a conduit which is arranged to be fed alternately with a gas sample flow by one or other of two secondary gas sample pumps, each of which is arranged to extract a partial gas flow from a respective one of the gas pipes, the conduit leading to conditioning units for the gas sample flow and hence to at least one gas analysing unit of the gas analyzing station for sensing the concentration of the gaseous component in the gas sample flow; a first detector for ensuring that gas from at least one of the extraction probes arrives at the analysing station and a second detector for ensuring that a partial gas flow passes through the gas analysing unit, the first detector functioning in cooperation with the second detector for ensuring that the prescribed partial sample flow of gas from the main sample of gas is fed to the analyzing station.

The equipment may also have a set of three-way valves for ensuring that the gas sample flow is always fed by that one of the gas sample pumps associated with the unblocked gas pipe.

The primary gas pump may advantageously be an ejector pump, and the secondary gas sample pumps may be diaphragm pumps. Both pump types are robust and can stand hot and corrosive gases. The ejector pump needs to have a big pump capacity. This is important as the latter pump solely extracts a main sample of gas to be transported with a very high velocity to the analyzing system while the gas to be analyzed is taken out of the main sample as a considerably smaller partial sample flow of gas to be fed to the conditioning and analyzing units of the analyzing station.

The measuring equipment may be provided with an alarm which is operated when a gas concentration sensed by an analysing unit exceeds a predetermined level, or if one of the detectors detects a loss of gas flow. In addition to the alarm, predetermined safety measures may be activated.

BRIEF DESCRIPTION OF THE DRAWINGS

The invention will now be explained in more detail, with reference to the accompanying drawings, in which.

DESCRIPTION OF THE PREFERRED EMBODIMENT

Figure 1:
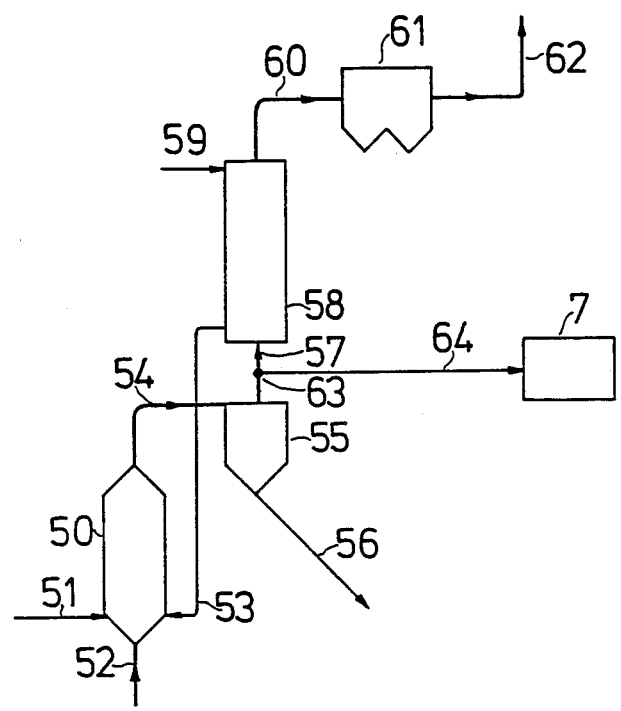
FIG. 1 is a diagrammatic representation of a calcining plant, showing the point of extraction of flue gas to be analysed in the equipment; and, FIG. 2 is a diagrammatic representation of monitoring equipment according to the invention.

FIG. 1 shows diagrammatically a material heat treatment plant in which raw material is treated in a calciner 50 which is supplied with fuel through a pipe 51 and with oxygen containing air through a pipe 52. Preheated material from a preheater 58 is passed through a pipe 53 to the calciner 50.

Flue gas, in which the calcined material is suspended, leaves the calciner 50 through a pipe 54 leading to a separating cyclone 55, in which the treated material is separated from the flue gas. Separated material leaves the cyclone 55 through a material outlet 56, while the flue gas leaves through a pipe 57 leading to the preheater 58, in which raw material supplied through a pipe 59 is preheated by the hot flue gas. The latter having given off part of its heat to the raw material, leaves the preheater through a pipe 60 and passes to an electrostatic precipitator 61, from where it is discharged into the open air through a chimney 62.

The flue gas extractors of the equipment according to the invention are mounted in the flue gas stream at the location 63 of the pipe 57. The line 64 represents a pair of gas pipes 3 and 4 shown in FIG. 2 feeding extracted gas to an analysing station 7.

If an undesired high concentration of combustible gases in the flue gas is detected at the location 63 the power supply to the electrostatic precipitator is interrupted before the explosive gas mixture reaches the precipitator via the preheater.

Detection of an explosive gas mixture may also activate other explosion counter-measures, e.g. cutting off of the fuel supply for the calciner.

Figure 2:
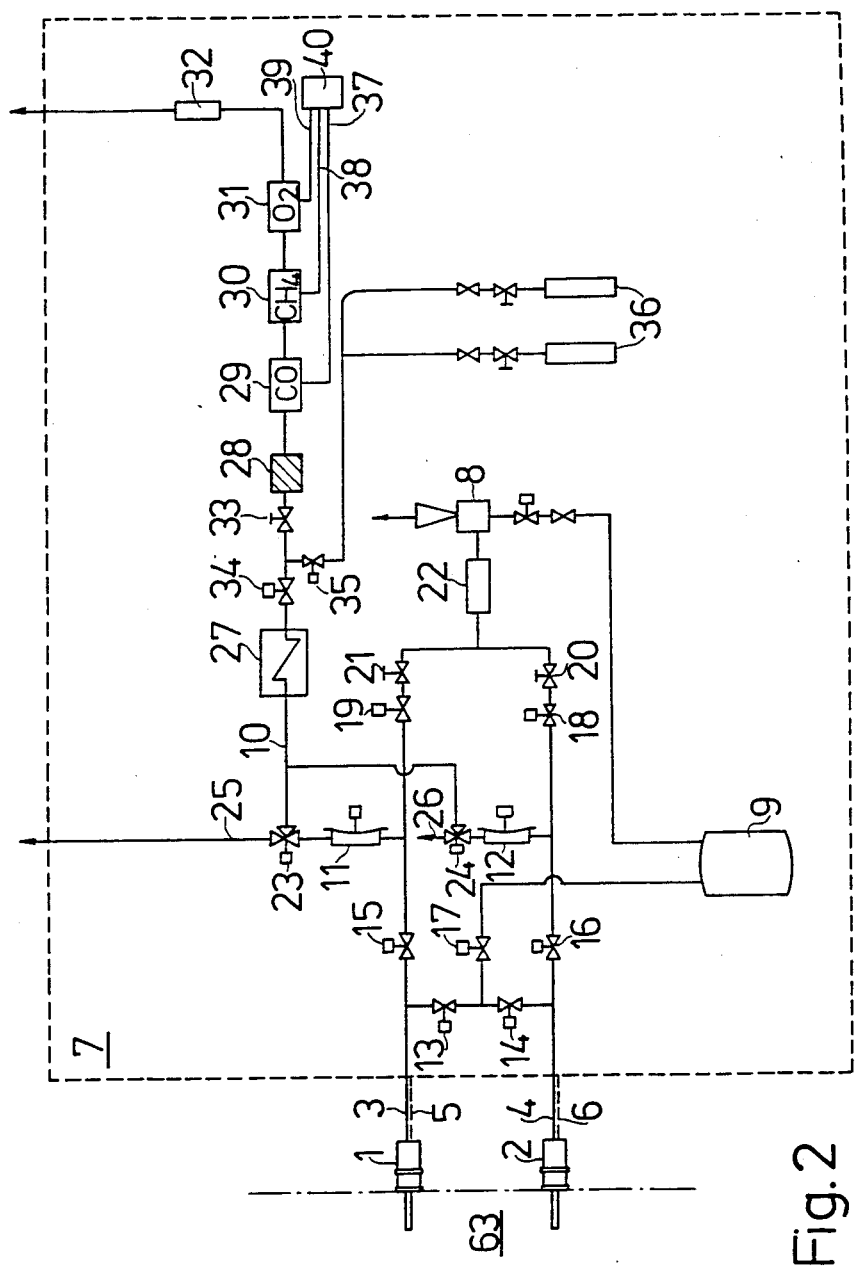

In the equipment shown in FIG. 2 a gas, the content, e.g. of CO, $CH_4$ and $O_2$, of which is to be monitored, is sucked through a pair of gas extraction probes 1 and 2.

From the respective probes 1 and 2 gas is led to the analysing station 7 through the gas pipes 3 and 4 and heated by heating elements 5 and 6 to avoid condensation of water in the pipes.

The extracted gas is sucked to the analysing station 7 by an ejector pump 8, driven by compressed air from a tank 9, which is kept under pressure by a compressor device (not shown).

By using a pump having a pump capacity which is big in relation to the volume of gas contained in the gas probes and gas pipes it is ensured that gas extracted by the probes reaches the analysing station in a very short time, of the order of a few seconds.

A sample of the gas led to the analysing station through the gas pipes 3 and 4 is extracted by diaphragm pumps 11 and 12, each connected to a respective one of the gas pipes 3 and 4, and is pumped through a conduit 10 into an analysing part 27 to 32 of the station where the analyses proper are performed.

By using two gas extraction probes it is possible alternately to blow one of them clean, the necessary gas extraction taking place through the other.

The gas probe 1 and its built-in dust filter are blown clean with a first set of valves 13 and 17 open, so that compressed air from the compressed air tank 9 is fed to the gas pipe 3. Simultaneoulsy, a second set of valves 15 and 19 close so that the compressed air is prevented from entering the analysis part 27 to 32.

When cleaning the gas probe 1, gas is sucked through the gas probe 2, the gas pipe 4 and the valves 16, 18 and 20 to the pump 8.

When cleaning the gas probe 2, gas is sucked through the gas probe 1, through the gas pipe 3 and valves 15, 19 and 21 to the pump 8.

The valves 16 and 18 are solenoid valves which are closed when the gas probe 2 is to be blown clean, while the valve 20 is a manually adjustable valve for adjusting the gas flow through gas pipe 4. Correspondingly, the valves 15 and 19 are solenoid valves which are closed when the gas probe 1 is to be blown clean, while the valve 21 is a manually adjustable valve.

A flow detector 22 senses the gas feed to the pump 8 and thereby that gas is being sucked through at least one of the gas probes 1 and 2.

Gas samples to be analysed are extractd from the gas pipes 3 and 4 by means of the diaphragm sample gas pumps 11 and 12 and are passsed through three-way valves 23 and 24, respectively, to the conduit 10 or to the atmosphere through the exit duct 25 and 26, respectively.

The three-way valves 23 and 24 ensure that the gas sample passed to the conduit 10 is always extracted from whichever of the gas pipes 3 or 4 is not being blown clean. Gas extracted from the pipe being blown clean is passed to the atmosphere. Immediately after a blowing sequence, when a pipe is reopened for gas throughflow from the gas probe 1 or 2 to the pump 8, the gas sample from the pipe in question is discharged until remains of the blow air have been totally sucked away by the pump 8.

The gas sample supplied to the conduit 10 is passed through a gas cooler 27 for conditioning the dew point of the gas to a preselected value. In a subsequent heating unit 28 the gas sample is heated to the analysing temperature above the dew point. The thus conditioned flue gas is subsequently analysed with regard to CO, CH$_4$ and O$_2$ in a number of analysing units 29, 30 and 31 before it leaves the analysing part via a flow detector 32, which senses that gas is passing through the analysing units, when the equipment is in operation. The gas flow through the analysing units 29-31 is regulated by a manually operated valve 33.

The equipment may be calibrated by cutting off the flue gas extracting from the analysing unit by closing a valve 34 and opening another valve 35 for supply of a calibrating gas of known composition from a number of gas cylinders 36.

The results from the respective analysing units 29, 30 and 31 are transformed in known ways into electric signals on output lines 37, 38 and 39. These signals may be used in various ways. Thus signals indicating that the content of combustible gases, CO or CH$_4$, exceeds a preselected level may operate an alarm 40, or interrupt the current supply for the electrostatic precipitator of the plant, while a signal indicating the O$_2$ content of the gas flow may be used for controlling the fuel supply for the plant.

The alarm and/or the interruption of the electrostation precipitator may also be actuated if one of the detectors 22 or 32 detects a malfunctioning of their respective equipment parts.

I claim:

1. In equipment for monitoring the amount of at least one gaseous component in a gas flow comprising two gas extraction probes which are adapted to extract a main sample of gas from substantially the same location in the gas flow, each probe having its own gas pipe leading to an analyzing station having conditioning means and gas analyzing units, a primary gas pump which is adapted to suck the main sample of gas from the probes to the analyzing station, a conduit leading the main sample of gas from the probe gas pipes to the analyzing station, detector means for ensuring that the main sample of gas from the extraction probes arrives at and passes through the analyzing station, and two secondary gas sample pumps, each of which is connected to a respective one of said probe gas pipes such that at least one of said secondary gas pump works simultaneously with the primary gas pump, and is adapted to extract from the sucked main sample of gas in the respective one of said probe gas pipes a partial sample flow of gas for feeding said partial sample to said conditioning means and to at least one gas analyzing unit of the analyzing station for sensing the concentration of the gas component in said partial sample flow of gas.

2. Equipment according to claim 1 wherein said conditioning means includes at least one conditioning unit for cooling and/or heating the gas sample to the analyzing temperature of the analyzing station, said conditioning units being an integrated part of said analyzing station, thus causing only the partial gas sample flow fed to the analyzing station by the secondary pumps to be subjected to conditioning in said conditioning units.

3. Equipment according to claim 1 or 2 further including a set of valves which are adapted to block the connection of one or other of said probe gas pipes alternately to said primary gas pump and to connect said blocked pipe to a compressed air system for blowing clean said probe of the respective one of said gas pipes.

4. Equipment according to claim 1 and 2 wherein said detector means includes a detector for ensuring that the prescribed main sample flow of gas is sucked through a respective one of said probe gas pipes, said detector functioning in cooperation with another detector for ensuring that the prescribed partial sample flow of gas from the main sample flow is fed to the analyzing station.

5. Equipment according to claim 3 wherein said detector means includes a detector for ensuring that the prescribed main sample flow of gas is sucked through a respective one of said probe gas pipes, said detector functioning in cooperation with another detector for ensuring that the prescribed partial sample flow of gas from the main sample flow is fed to the analyzing station.

6. Equipment according to claim 3 further including a set of three-way valves for ensuring that said partial sample flow of gas is always fed to the analyzing station by that one of said secondary gas sample pumps not associated with the blocked one of said probe gas pipes.

7. Equipment according to claim 4 further including a set of three-way valves for ensuring that said partial sample flow of gas is always fed to the analyzing station by that one of said secondary gas sample pumps not associated with the blocked one of said probe gas pipes.

* * * * *